US012576053B2

(12) United States Patent
Tomulewicz

(10) Patent No.: US 12,576,053 B2
(45) Date of Patent: Mar. 17, 2026

(54) USE OF 2-[(3Z)-6-FLUORO-2-METHYL-3-[(4-METHYLSULFINYLPHENYL) METHYLIDENEJINDEN-1-YL] ACETIC ACID

(71) Applicant: WYŻSZA SZKOŁA MEDYCZNA W BIAŁYMSTOKU, Białystok (PL)

(72) Inventor: Mikołaj Tomulewicz, Białystok (PL)

(73) Assignee: WYSZA SZKOA MEDYCZNA W BIAYMSTOKU, bIALYSTOK (PL)

( * ) Notice: Subject to any disclaimer, the term of this patent is extended or adjusted under 35 U.S.C. 154(b) by 0 days.

(21) Appl. No.: 16/606,739

(22) PCT Filed: Apr. 11, 2018

(86) PCT No.: PCT/PL2018/000036
§ 371 (c)(1),
(2) Date: Oct. 19, 2019

(87) PCT Pub. No.: WO2018/203762
PCT Pub. Date: Nov. 8, 2018

(65) Prior Publication Data
US 2020/0129459 A1      Apr. 30, 2020

(30) Foreign Application Priority Data
May 4, 2017    (PL) ..................................... P.421491

(51) Int. Cl.
*A61K 31/192*          (2006.01)
*A61P 17/02*           (2006.01)
(52) U.S. Cl.
CPC ............ *A61K 31/192* (2013.01); *A61P 17/02* (2018.01)
(58) Field of Classification Search
CPC ............................... A61K 31/192; A61P 17/02

USPC .......................................................... 514/570
See application file for complete search history.

(56) References Cited

U.S. PATENT DOCUMENTS 6,187,822 B1 * 2/2001 Leibovich .............. A61K 31/05
514/456
2012/0295979 A1 11/2012 Prentice

FOREIGN PATENT DOCUMENTS

WO      WO-0185983 A2 * 11/2001 ........ A61K 49/0004
WO      WO-2009137400 A2 * 11/2009 .............. A61P 31/00
WO      2011088474 A2    7/2011

OTHER PUBLICATIONS

Ratliff D M et al: "Inhibition of Human Aldose and Aldehyde Reductases by Non-Steroidal Anti-Inflammatory Drugs", Retinal Degenerative Diseases: Advances in Experimental Medicine and Biology;US, vol. 463, pp. 493-499 (Year: 1999).*

(Continued)

*Primary Examiner* — Deborah D Carr
(74) *Attorney, Agent, or Firm* — Andrzej Malarz, Esq.

(57) ABSTRACT

A new use of 2-[(3Z)-6-fluoro-2-methyl-3-[(4-methylsulfi-nylphenyl)methylidene]inden-1-yl] acetic acid (sulindac) of the formula 1 for making the pharmaceutical preparations for the treatment of difficult healing different types of wounds in patients with diabetes.

Figure 2:
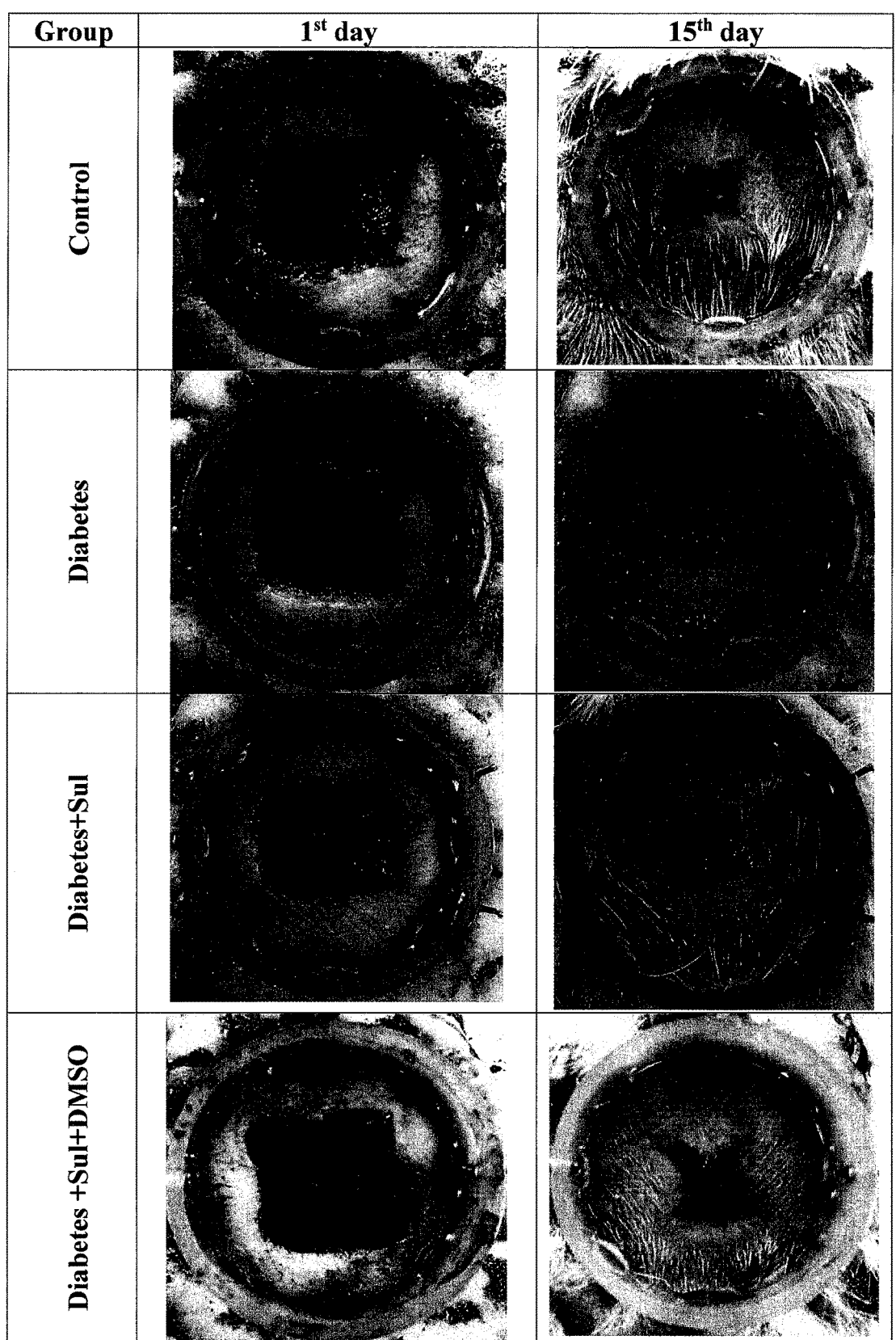

The medical use of 2-[(3Z)-6-fluoro-2-methyl-3-[(4-meth-ylsulfinylphenyl)methylidene]inden-1-yl] acetic acid (sulin-dac) of the formula 1 shown in the FIG. 1 for the preparation of pharmaceutical formulations for the treatment of difficult healing different types of wounds in patients with diabetes is disclosed.

1 Claim, 5 Drawing Sheets

Formula 1

(56)                    References Cited

OTHER PUBLICATIONS

M Jacobson: "Diabetic complications in lens and nerve and their prevention by sulindac or sorbinil: two novel aldose reductase inhibitors", IOVS, vol. 24, No. 10, pp. 1426-1429 (Year: 1983).*

Sharma Y. R et al. "Topical sulindac therapy in diabetic senile cataracts: cataract IV." Indian Journal of Ophthalmology 1989, 37(3), pp. 127-133.

Hattori Y. et al. "The effect of long-term treatment with sulindac on the progression of diabetic retinopathy." Curr Med Res Opin. 2007, 23(8), pp. 1913-1917.

Kata M. K. et al. "The influence of sulindac on diabetic cardiomyopathy: A non-invasive evaluation by Doppler echocardiography in streptozotocin-induced diabetic rats.", Vascular Pharmacology 2005, 43, pp. 91-100.

Walker D. et al. "Nerve pathology in the type 1 diabetic dog: effects of treatment with sulindac.", Journal of the Peripheral Nervous System 2001, 6(4), pp. 219-226.

Friederich P. et al. "Effects of intervention with sulindac and inulin/VSL#3 on mucosa! and luminal factors in the pouch of patients with familial adenomatous polyposis". Int. J. Colorectal Dis., 2011; 26: pp. 575-582.

Lee Y.S. et al. "CXCR2 inhibition enhances sulindac-mediated suppression of colon cancer development". Int. J. Cancer., 2014; 135: pp. 232-237.

Li X. et al. "Sulindac sulfide inhibits colon cancer cell growth and downregulates specificity protein transcription factors" BMC Cancer, 2015; 15: p. 974 (breast cancer).

Tinsley H.N. et al. "Sulindac sulfide selectively inhibits growth and induces apoptosis of human brest tumor cells by phosphodiesterase 5 inhibition, elevation of cyclic GMP, and activation of protein kinase" G. Mol. Cancer Ther., 2009; 8: pp. 3331-3340 (prostate cancer).

Du J. et al. "Anticancer activities of sulindac in prostate cancer cells associated with c-Jun NH2-terminal kinase 1/β-catenin signaling" Oncol. Lett., 2014; 8: pp. 313-316.

Femia A.P. et al. "Sulindac, 3,3••diindolylmethane and curcumin reduce carcinogenesis in the Pirc rat, an Ape-driven model of colon carcinogenesis" BMC Cancer, 2015; 15: p. 611.

Alshahrani S. et al. "Rapid determination of the thermal nociceptive threshold in diabetic rats" J Vis Exp., 2012; (63): e3785].

* cited by examiner

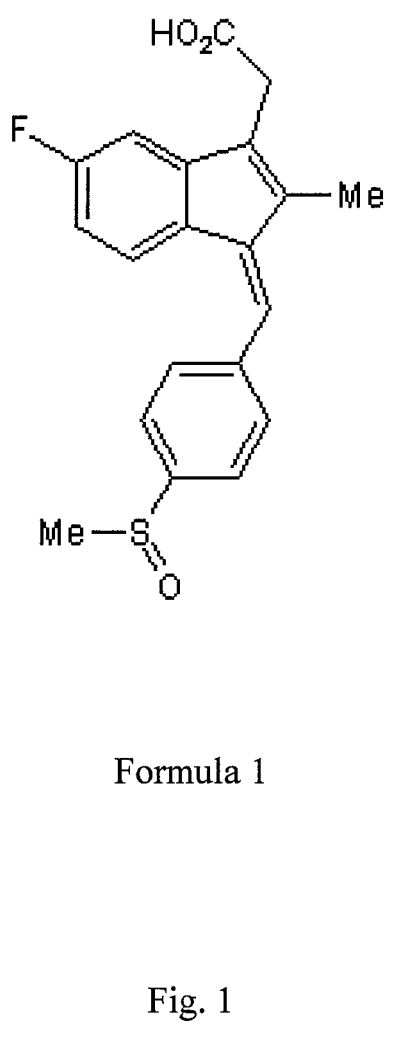

Formula 1

Fig. 1

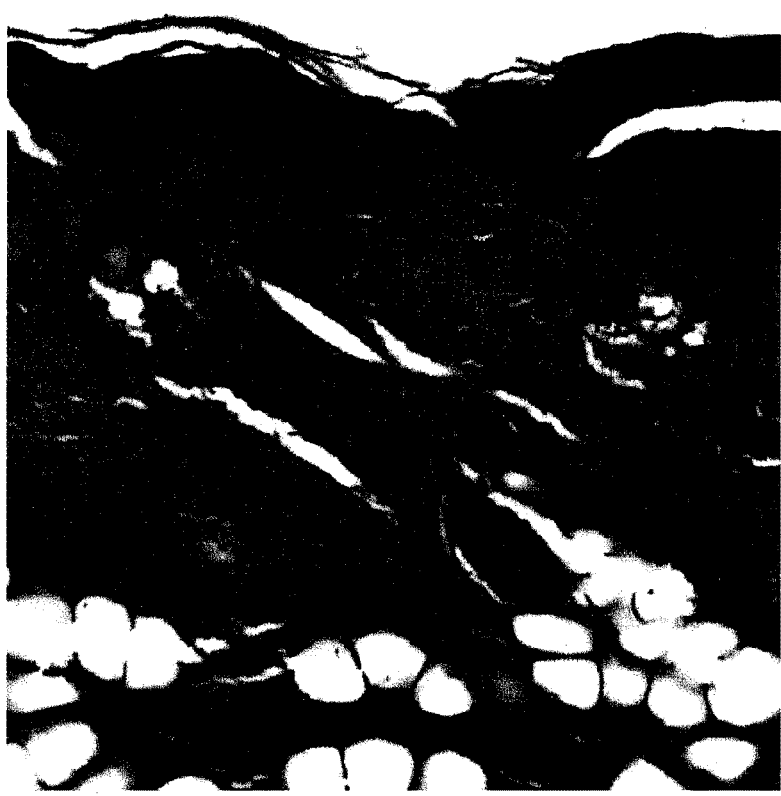
Fig. 3 – Symptoms of necrosis of the epidermis and reticular layer of the dermis. Dyeing H+E, magnification x 400.
Fig. 4 – Inflammatory infiltration zone. Dyeing H+E, magnification x 400.

Fig. 5 – The structure of the skin on the edge of damage. Dyeing H+E, magnification x 100.
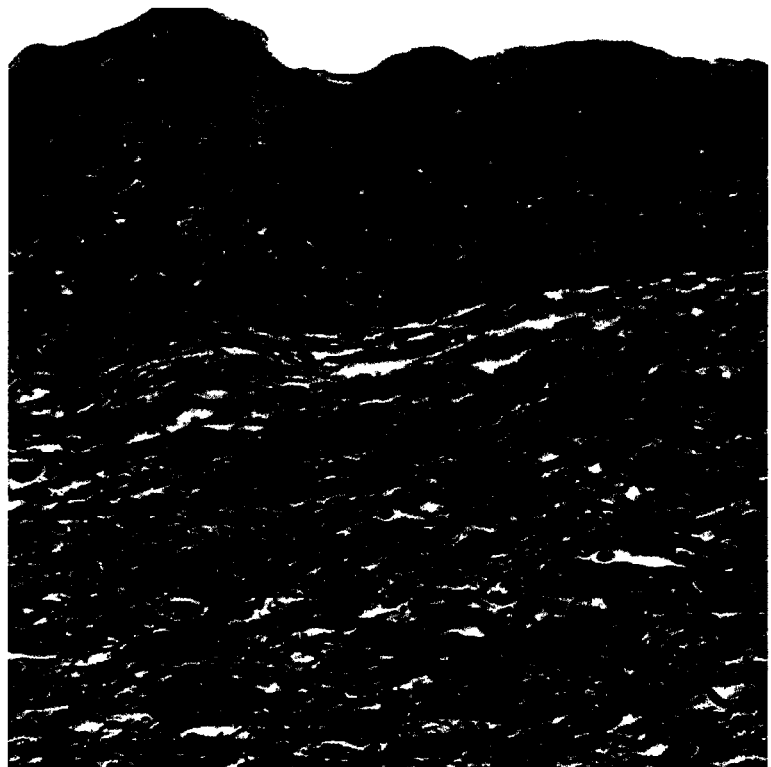
Fig. 6 – Connective scar tissue and epidermis covering it. Dyeing van Gison, magnification x 400.

Fig. 7 – The structure of the skin on the edge of damage (wound). Dyeing H+E, magnification x 100.
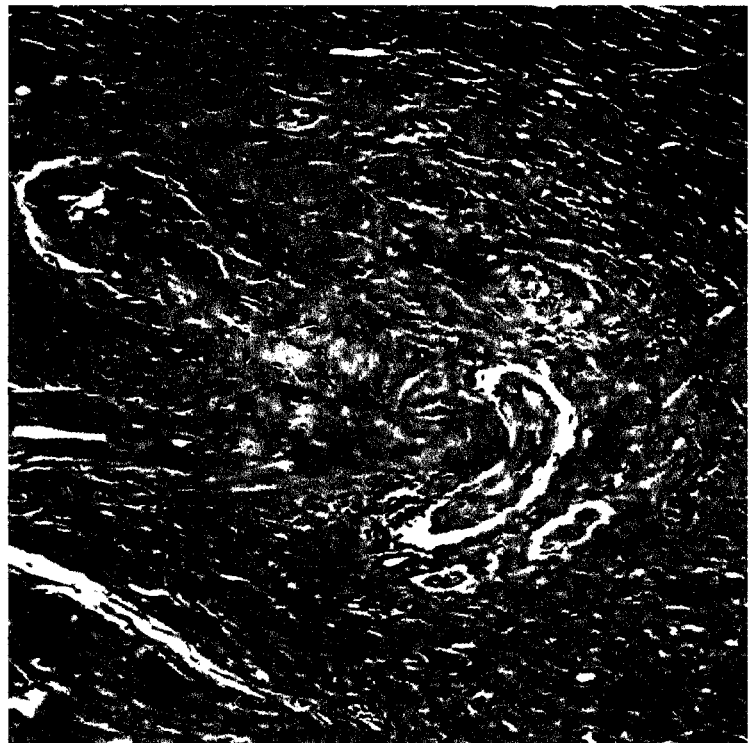
Fig. 8 – Skin products appearing on the edge of the lesion. Dyeing H+E, magnification x 100.

USE OF 2-[(3Z)-6-FLUORO-2-METHYL-3-[(4-METHYLSULFINYLPHENYL) METHYLIDENEJINDEN-1-YL] ACETIC ACID

The present invention relates to a new use of 2-[(3Z)-6-fluoro-2-methyl-3-[(4-methylsulfinylphenyl)methylidene] inden-1-yl] acetic acid (sulindac) of the formula 1 to making of pharmaceutical preparations for the treatment of difficult healing different types of wounds in patients with diabetes.

The basis for developing the invention is providing patients and doctors (diabetologists, surgeons) with new preparations that have a beneficial effect on the wound healing process (of various origins) in patients with diabetes.

Pharmaceutical formulations containing 2-[(3Z)-6-fluoro-2-methyl-3-[(4-methylsulfinylphenyl)methylidene]inden-1-yl] acetic acid (sulindac) are commercially available as non-steroidal anti-inflammatory drugs that inhibit the cyclooxygenase enzyme 1 (COX-1), thereby reducing the production of prostaglandins, which translates into their analgesic effect. The preparations available on the pharmaceutical market are Klinoril, Clinoril, Sudaclin. These compounds can be prepared by conventional methods.

According to the definition of the World Health Organization (WHO), diabetes (Latin: Diabetes mellitus, literally: honey leak) is a chronic metabolic disease characterized by a high level of blood glucose, the so-called hyperglycemia. It is the result of an absolute or relative deficiency of insulin. According to the WHO, currently 422 million people suffer from diabetes, of which half are not diagnosed. In Poland, the number of patients is estimated at approximately 3.5 million, of which ⅓ are still not diagnosed. All global and Polish reports indicate a further increase in the number of cases. In Poland, diabetes is still the main cause of blindness in adults, kidney failure and limb amputation. This pathology is also a major risk factor for ischemic heart disease and myocardial infarction and a very common cause of stroke, diabetic foot syndrome and amputation, as well as congenital defects of newborns.

The classification of diabetes includes several types depending on the cause and course of the disease. There is type 1 diabetes, where the insulin deficit results from the destruction of the β cells of the Langerhans islets of the pancreas, usually as a consequence of an autoimmune disease; type 2 diabetes, which is the most common type of diabetes in which a relative insulin deficiency or insulin resistance is observed; other specific types of diabetes such as pancreatic diabetes (caused by pancreatitis associated with pancreatic islet destruction or toxin-damaging cells), steroid diabetes (due to increased release of hormones acting antagonistically to insulin, e.g. in the course of Cushing's disease), gestational diabetes (effect of increased secretion of insulin antagonists: placental lactogen, chorphomatous somatomammotropin, estrogen, progesterone and prolactin).

Metabolic disorders occurring in the course of diabetes may lead to serious and irreversible changes in the body. Hyperglycemia plays a major role in this process.

Long-lasting hyperglycemia leads to increased activation of the polyol pathway. Glucose is reduced to sorbitol in cells that contain the enzyme aldose reductase. This leads to the accumulation of sorbitol, which is a polyol, an intermediate product of the conversion of glucose to fructose. Glucose is reduced to sorbitol, and then sorbitol is oxidized to fructose. In the conditions of prolonged hyperglycemia, this process intensifies, causing, e.g. deposition of sorbitol in axons, swelling and damage to Schwann cells (demyelination), disrupts nerve conduction (polyneuropathy). Accumulation of sorbitol in the lens of the eye causes the subsequent retention of water in it, leading to the development of cataracts. Hyperglycemia intensifies the formation of plasma proteins containing sugars, such as fibrinogen, haptoglobin, or coagulation factors V and VIII, leading to an increase in blood viscosity and an increased risk of thrombosis. Long-lasting hyperglycemia results in the binding of glucose to free amino groups of proteins, resulting in compounds—advanced glycation end products (AGE), whose concentration increases with age and may lead to nephropathy or diabetic microangiopathy. When the blood glucose is too high, the cells of the immune system are not working properly. The production of enzymes and cytokines by them is disrupted.

Chronic hyperglycemia may lead to the formation of various types of difficult to heal wounds, including ulcers and diabetic foot. Feet and ankles are particularly prone to complications associated with the difficult process of healing wounds. This is due to the fact that the dynamics of the healing process below the knees is slightly different than in the rest of the body. This is the result of, among others susceptibility of this area of the body to the formation of oedemas that hinder healing process. In addition, the factors that contribute to the development of foot wounds in diabetics are the above mentioned nerve damage and disturbed nerve conduction (neuropathies) and circulatory disorders (microangiopathies). Weakened sensation causes wound sores to be noticed later by patients. What's more, the wounds can become infected and their healing becomes even more difficult.

In the current clinical practice, special gels or hydrogel dressings are used for the podiatrically prepared wound, which only provide the optimal environment in it, thus accelerating the healing process. The dressing adheres tightly to the wound, preventing additional infection. In addition, an infected antibiotic or bactericide is used for infected wounds. The wounds can be protected with active dressings, which, for example, absorb excessive exudate or smell, e.g. silver-carbon dressings or have only antibacterial effects like silver dressings.

Non-steroidal anti-inflammatory drugs (NSAIDs) are one of the most commonly used by patients and the most commonly prescribed group of medications. Their analgesic, anti-inflammatory and antipyretic properties are well known. The mechanism of action of the entire broad NSAID group, including 2-[(3Z)-6-fluoro-2-methyl-3-[(4-methylsulfinylphenyl)methylidene]inden-1-yl] acetic acid (sulindac), is based on affinity this group of drugs for cyclooxygenase (COX) leading to inhibition of catalytic activity of this enzyme, and thus inhibition of the production of precursors of pro-inflammatory mediators—prostaglandins and thromboxanes.

Two cyclooxygenases are known. COX-1 is found constitutively in most cells, while COX-2 is induced and its expression depends on the type of stimulus to be activated. COX-2 is a direct product of early response genes, the amount of which increases under the influence of stress, growth factors, carcinogens and cytokines. COX-1 forms prostanoids involved in the maintenance of homeostasis. COX-2 is the main source of prostanoids in inflammation and cancer. NSAIDs exert their effects by inhibiting cyclooxygenases. Indomethacin and 2-[(3Z)-6-fluoro-2-methyl-3-[(4-methylsulfinylphenyl)methylidene]inden-1-yl] acetic acid (sulindac) are more selective for COX-1.

2-[(3Z)-6-fluoro-2-methyl-3-[(4-methylsulfinylphenyl) methylidene]inden-1-yl] acetic acid (sulindac) is a sulfoxide prodrug that is reversibly converted into the active sulphide metabolite. It is secreted into the bile and then absorbed from the intestine.

2-[(3Z)-6-fluoro-2-methyl-3-[(4-methylsulfinylphenyl) methylidene]inden-1-yl] acetic acid (sulindac) is indicated in rheumatoid diseases. It also inhibits the development of familial intestinal polyposis [Friederich P. and co-workers: Effects of intervention with sulindac and inulin/VSL #3 on mucosal and luminal factors in the pouch of patients with familial adenomatous polyposis. Int. J. Colorectal Dis., 2011; 26: 575-582] and probably the development of colon cancer [Lee Y. S. and co-workers: CXCR2 inhibition enhances sulindac-mediated suppression of colon cancer development. Int. J. Cancer., 2014; 135: 232-237; Li X. and co-workers: Sulindac sulfide inhibits colon cancer cell growth and downregulates specificity protein transcription factors. BMC Cancer, 2015; 15: 974] breast cancer [Tinsley H. N. and co-workers: Sulindac sulfide selectively inhibits growth and induces apoptosis of human breast tumor cells by phosphodiesterase 5 inhibition, elevation of cyclic GMP, and activation of protein kinase G. Mol. Cancer Ther., 2009; 8: 3331-3340] and prostate cancer [Du J. and co-workers: Anticancer activities of sulindac in prostate cancer cells associated with c-Jun NH2-terminal kinase 1/β-catenin signaling. Oncol. Lett., 2014; 8: 313-316]. In the form of sulfone (rarely sulphide) seems to decrease the incidence of gastrointestinal cancers in rats [Femia A. P. and co-workers: Sulindac, 3,3'-diindolylmethane and curcumin reduce carcinogenesis in the Pirc rat, an Apc-driven model of colon carcinogenesis. BMC Cancer, 2015; 15: 611].

From the American patent US 20120295979 A1 is known the use of sulindac, i.e. 2-[(3Z)-6-fluoro-2-methyl-3-[(4-methylsulfinylphenyl)methylidene]inden-1-yl] acetic acid, for the protection of retina epithelial cells before oxidative stress, which is the main cause of macular degeneration leading to loss of eyesight.

From the international patent WO 2011088474 A2 is known the use of sulindac, i.e. 2-[(3Z)-6-fluoro-2-methyl-3-[(4-methylsulfinylphenyl)methylidene]inden-1-yl] acetic acid and its sulphonic derivatives for the treatment of rhinovirus respiratory infections by inhibiting or reducing the number of replication cycles of the virus, thus preventing the spread of infection.

Recent research indicates that these beneficial NSAIDs do not fully exploit their therapeutic potential.

The essence of this invention is a new medical application 2-[(3Z)-6-fluoro-2-methyl-3-[(4-methylsulfinylphenyl) methylidene]inden-1-yl] acetic acid (sulindac) of formula 1, shown in the drawing, to making of pharmaceutical preparations for the treatment of difficult healing different types of wounds in patients with diabetes.

The essence of the present invention is also a pharmaceutical composition comprising 2-[(3Z)-6-fluoro-2-methyl-3-[(4-methylsulfinylphenyl)methylidene]inden-1-yl] acetic acid (sulindac) of formula 1 in combination with at least one a pharmaceutical carrier, applicable to the treatment of difficult healing different types of wounds in patients with diabetes.

These compositions can be prepared by conventional methods. Dosage unit forms may contain from 1 mg to 200 mg of substance of formula 1.

Surprisingly, it was found that 2-[(3Z)-6-fluoro-2-methyl-3-[(4-methylsulfinylphenyl)methylidene]inden-1-yl] acetic acid (sulindac) exerts a beneficial effect on the healing process of injured skin patients with diabetes when applied directly to the wound.

For the treatment of damaged skin in diabetic patients, 2-[(3Z)-6-fluoro-2-methyl-3-[(4-methylsulfinylphenyl) methylidene]inden-1-yl] acetic acid (sulindac) can be used as usual pharmaceutical formulations administered to the skin. Thus, 2-[(3Z)-6-fluoro-2-methyl-3-[(4-methylsulfinylphenyl)methylidene]inden-1-yl] acetic acid (sulindac) may be included in solid, semi-solid or liquid pharmaceutical formulations in an active quantity, leading to recovery (complete healing of the damaged skin) along with ordinary pharmaceutical adjuvants and carriers. As examples of preparations in a liquid form, solutions of different viscosities should be mentioned, administered directly to the damaged skin. These pharmaceutical formulations may contain viscosity enhancers such as, e.g. methylcellulose, carboxymethylcellulose, hydroxypropylcellulose, gum arabic, tragacanth, sodium alginate, gelatin, carbomer, bentonite. In addition, they may contain solvents such as, e.g. water, alcohols or glycols, and stabilizers (polysorbate, Cremophor®) or antioxidants (pyrosulfate sodium, ascorbic acid).

The formulations of the active compounds with pharmaceutical adjuvants and/or carriers can be mixed and prepared in a known manner. In order to prepare the formulation in the liquid form its necessary mixed the appropriate amount of one or more of the thickeners with water, allowed to be deaerated and then the active substance added. The composition can be supplemented with the addition of stabilizing and antioxidant compounds.

EXAMPLE

Use of 2-[(3Z)-6-fluoro-2-methyl-3-[(4-methylsulfinylphenyl)methylidene]inden-1-yl] acetic acid (sulindac) for the treatment of difficult healing wounds in rats with alloxan-induced diabetes.

Methods 63 adult male Wistar rats were used in in the experiment. All animals were kept under observation for two weeks before the onset of the experiment to exclude any intercurrent infection. Animals were housed in standard plastic cages by 5 animals per cage. Rats were kept in air-conditioned room at $22\pm2°$ C., humidity of 60-70% and a natural light (12/12 in the day/night cycle). All rats were fed ad libitum with standard laboratory rats chow.

Induction of Diabetes Mellitus

Diabetes mellitus was induced with alloxan, a highly toxic compound that destroyed the β-cells of the pancreas Langerhans islets, by single intraperitoneally injection at dose 170 mg per kg of body weight in 0.1 M citrate-phosphate buffer, pH 4.0 after 24-hours fasting. After alloxan administration drinking water was replaced by 2 percent sucrose solution in tap water on 10 days period.

Rats were identified as diabetic on the basis of blood glucose levels (higher than 16 mmol/l after 12 h starvation at 10 days post-alloxan treatment; total 31 rats were diabetic).

Determination of the Thermal Nociceptive Threshold

Thermal nociceptive threshold of each diabetic rat was tested three month later after diabetes induction as described by Alshahrani et al. (2012) to identify altered sensory processing in rats [Alshahrani S. and co-workers: Rapid determination of the thermal nociceptive threshold in diabetic rats. J Vis Exp., 2012; (63): e3785].

Estimation of Blood Glucose Level and Glycosylated Haemoglobin

Blood glucose levels were estimated using Roche Accu Check Active glucometer and corresponding glucose test strips. Glycosylated haemoglobin levels were determined using Clover A1c analyzer and appropriate kit.

Induction of Excision Wounds

Each experimental group was equalized to average blood glucose, glycosylated haemoglobin and thermal nociceptive threshold.

Each rat was anesthetized with chloral hydrate (300 mg per kg of b/w) and the fur on dorsal area was pulled out manually. The surgical field was treated with 70% ethanol. In the center of upper part of dorsum, in scapulary region, a square-shaped piece of skin ~1 sq. cm. was excised. After that ring-shaped sterile limiter (8 mm high, 20 mm in diameter) was fixed on the side of the dorsal midline and sewed with silk sutures.

Immediately after the procedure, analgesia with sodium metamizole (40 mg/kg) was performed intramuscularly. Analgesic treatment was maintained for three consecutive days with metamizole at 200 mg/kg per os.

Treatment of Wounds and Sampling

As medication were used 2-[(3Z)-6-fluoro-2-methyl-3-[(4-methylsulfinylphenyl)methylidene]inden-1-yl] acetic acid (sulindac) (Sul) and 2-[(3Z)-6-fluoro-2-methyl-3-[(4-methylsulfinylphenyl)methylidene]inden-1-yl] acetic acid (sulindac)+DMSO (Sul+DMSO) solutions for experimental animals, and physiological saline for control group. All solutions (200 µl/daily, until full healing) were applied directly on the wound surface. After that sterile gauze was used for wound covering.

Every day wounds were irrigated with equal volume of 0.05% chlorhexidine solution before treatment procedure to minimize wound contamination and infection.

Nursing was performed under ether anesthesia. During nursing, 3, 5 and 7 days after wounding, the chamber cavity was washed with 1 ml of sterile saline. These rinse waters were used for immunological studies.

Dynamics of Epithelialization and Wound Contraction

Every day wounds were photographed by digital camera. Wound macroscopic parameters were quantified using the ImageJ software (NIH, USA).

Degree of epithelization ($S_1$) was calculated as follows:

$$S_1 = \frac{S_{ep}}{S_{wound}} \times 100\%, \quad (1)$$

where $S_{ep}$—epithelium area, $S_{wound}$—wound surface area at the given terms of healing.

Relative wound sizes ($S_2$) are expressed as percentage of the initial area of wound:

$$S_2 = \frac{S_t}{S_0} \times 100\% \quad (2)$$

where $S_0$—initial area of wound, a $S_t$—area of wound at the given terms of healing.

Histology

Tissue specimens next day after full epithelization were excised in depth to include underlying connective tissues above the external fascia of the dorsal muscles. The excised skin was fixed in paraformaldehyde (4% in PBS, 0.01 M, pH 7.4), dehydrated in graded alcohol solutions, embedded in paraffin blocks and sectioned at 5 µm-thick serial sections using microtome.

Measurement of Rat Subcutaneous Muscle Aldose Reductase Activity

Tissue samples were homogenized in 135 mM Na, K-phosphate buffer (pH 7.0) containing 5 mM 2-mercaptoethanol. The homogenate was centrifuged at 12,000 g for 30 min and the supernatant was used in the following steps. Aldose reductase activity was determined according to the classic method with glyceraldehyde as substrate. The incubation mixture contained 135 mM Na, K-phosphate buffer (pH 7.0), 100 mM lithium sulfate, 0.03 mM NADPH, 0.04 mM D,L-glyceraldehyde (monomerized at 80 deg C. for 10 min and cooled to RT) as a substrate and the sample solution (50 µL). The reaction was initiated by adding NADPH at 37 C and stopped by adding 0.5 M HCl, followed by the addition of 6 M NaOH containing 10 mM imidazole. The solution was heated at 60 C for 10 min to convert NADP to a fluorescent product. The fluorescence was measured using a spectrofluorometer with ex/em 360/460 nm. The assay was performed in duplicates. Protein content was determined using BCA assay.

Extraction of Sorbitol from Tissue

Each muscle sample was cut into small pieces and ground in the presence of liquid nitrogen until it was powdered. The weight of the powered muscle tissue was determined, after which 1 mL of ice-cold 0.5 M perchloric acid was added and the samples were sonicated. The sonicated tissue was centrifuged for 5 min to remove precipitate. The resulting supernatant was neutralized by adding a solution 0.5 M potassium carbonate. The solution was then vortexed for 45 seconds, then centrifuged for 5 min at 5000 g and precipitate was discarded. The samples were stored in deep freezer at −86° C. until sorbitol determination.

Determination Procedure for Sorbitol in Muscle Tissue

The neutralized muscle extracts were vortexed and 10 µL aliquots along with sorbitol standards were added to a 96 well plate. Sorbitol dehydrogenase reaction was started by adding to each well 10 µL of a reaction mix containing 20 µg/µL sorbitol dehydrogenase, 2 mM NAD in 50 mM glycine-NaOH buffer pH 9.7. Following incubation with sorbitol dehydrogenase for 30 min at room temperature, 100 µL of a solution containing 65 µg/mL diaphorase, 10 uM FMN, 20 µM resazurin in 50 mM glycine-NaOH, pH 9.7 was added and the fluorescence (ex/em at 544/590 nm) was determined on a fluorescent plate reader for a period of an hour. Sorbitol content was expressed in nmol/mg of wet muscle weight.

Ethical Norms of the Use of Animals in Research

All experiments were conducted in accordance with the National Institute of Health Animal Care and Use Committee protocols (USA).

Statistical Processing

Statistical processing of experimental data carried out using a statistical software Graph Pad Prism v.6.0. The data in the tables presented as M±m, where M—mean value, m—standard error of mean, or as mediana ($25^{th}$ percentile; $75^{th}$ percentile). Statistical significance was evaluated using ANOVA and Tukey's post hoc test. Differences were considered statistically significant at a p-value <0.05.

Results

TABLE

| Parameters of diabetes in animals | | | | |
| --- | --- | --- | --- | --- |
| Group | N | Glucose mmol/l | Glycosylated Hb % | TNT, deg C. |
| Control | 5 | 4.67 ± 0.52 | 6.18 ± 0.54 | 50.4 ± 0.45 |
| Diabetes | 9 | 23.76 ± 1.41*** | 16.51 ± 0.38*** | 43.7 ± 0.34*** |
| Diabetes + Sul | 8 | 20.76 ± 1.50 | 16.72 ± 0.44 | 43.3 ± 0.43 |
| Diabetes + Sul + DMSO | 8 | 21.83 ± 1.73 | 15.64 ± 0.68 | 44.0 ± 0.38 |

***$p < 0.001$ compared to the control group.

TABLE

| Influence of medications on wound healing, sorbitol levels and activity of aldose reductase in subcutaneous muscle subjacent wound in rats | | | | |
| --- | --- | --- | --- | --- |
| Group | N | Full healing, days | Sorbitol levels, nmol/mg | AR, nmole NADPH/min/mg protein |
| Control | 5 | 15.4 ± 0.63 | 0.030 ± 0.001 | 0.76 ± 0.02 |
| | | 15.3(14.3; 16.6) | 0.030(0.028; 0.033) | 0.776(0.701; 0.802) |
| Diabetes | 7 | 26.6 ± 0.60 | 0.190 ± 0.025 | 6.91 ± 0.32 |
| | | 26.0(26.0; 27.0) *** | 0.21(0.12; 0.22) *** | 7.0(6.05; 7.79) *** |
| Diabetes + Sul | 7 | 23.7 ± 0.65 | 0.057 ± 0.005 | 0.64 ± 0.04 |
| | | 24.0(22.0; 25.0) ᐃ | 0.053(0.048; 0.075) ᐃᐃᐃ | 0.677(0.63; 0.69) ᐃᐃᐃ |
| Diabetes + Sul + DMSO | 7 | 21.9 ± 0.99 | 0.041 ± 0.006 | 0.40 ± 0.03 |
| | | 21.0(20.0; 25.0) ᐃᐃᐃ | 0.032(0.029; 0.061) ᐃᐃᐃ | 0.375(0.343; 0.47) ᐃᐃᐃ |

***$p < 0.001$ compared to the control group.
ᐃ$p < 0.05$,
ᐃᐃᐃ$p < 0.001$ analysis of ANOVA variance with Tukey's post hoc test.

Histology

Preparations from the collected skin fragments were prepared in a standard manner and stained with the classic method using hematoxylin and eosin, and by the van Gison method using picric acid and acid fuchsine. The preparations were analyzed using a Leica DM 1000 light microscope equipped with a Leica DFC300 FX digital camera.

Diabetes

In all areas of the sample, with the exception of the site of injury, the epithelium was normal, with visible layers, but in most areas there were necrotic changes of the epidermis and reticular layer of the dermis as well as subcutaneous muscle fibers near which there was an edema zone and inflammatory infiltration (FIG. 3).

In the wound area, the basal layer of the dermis is unformed connective tissue/mature granulation tissue. The dermis collagen bundles are swollen, translucent, heavily stained, and between them pycnotic fibroblast cores are located.

In the vessels of the subcutaneous tissue symptoms of erythrostasis and thrombosis were observed, often also hemorrhage into the subcutaneous tissue. Muscle fibers are devoid of the cell nucleus (or have "shadow" nuclei), myofibrils are contracted, and in the cytoplasm clearly cracks are visible. Edema and numerous macrophages, lymphocytes and neutrophils infiltrating connective tissue are also visible. Between the infiltrating macrophages, fragments of muscle fibers with edematous nuclei and homogeneous cytoplasm are visible. Muscle fibers lying deeper than the infiltration zone reaches have a normal structure (FIG. 4).

Diabetes+2-[(3Z)-6-fluoro-2-methyl-3-[(4-methyl-sulfinylphenyl)methylidene]inden-1-yl] acetic acid (sulindac)

In all areas of the intact area of the skin sample epidermis is normal, with all layers visible, with an unevenly thickened stratum corneum and granular zone. On the edges of the wounds the epidermis is infiltrated to a slight extent by single lymphocytes. In deep dermis layers, atherosclerotic blood vessels were observed (FIG. 5).

In the area of damage, the skin was rebuilt in the form of a scar tissue made of modified connective tissue, infiltrated slightly near the epidermal border by macrophages and single lymphocytes. On the surface of the lesion, the epidermis was established in the form of a straight-line coating in which all the characteristic layers are visible (FIG. 6).

Diabetes+2-[(3Z)-6-fluoro-2-methyl-3-[(4-methyl-sulfinylphenyl)methylidene]inden-1-yl] acetic acid (sulindac)+DMSO In all places, except the skin, the samples had a typical structure, epidermis was normal, with all layers visible. In the area of damage, the skin was rebuilt in the form of scar tissue from the modified connective tissue, infiltrated slightly near the epidermal border by macrophages and single lymphocytes, separate blood vessels proliferating in the skin were also observed (FIG. 7). On the surface of the lesion, the epidermis was established in the form of a straight-line coating in which all the characteristic layers are visible. On the edge of the lesion, in the subcutaneous region, numerous clusters of sebaceous gland-forming cells have been observed (FIG. 8).

Summary

2-[(3 Z)-6-fluoro-2-methyl-3-[(4-methylsulfinylphenyl)methylidene]inden-1-yl] acetic acid (sulindac) are commercially available as non-steroidal anti-inflammatory drugs, can be use new drug for the treatment difficult healing wounds in individuals with diabetes.

The invention claimed is:

1. A method of treating difficult healing various types of wounds and damaged skin in patients with diabetes with a pharmaceutical composition, wherein the composition comprises viscosity enhancers selected from the group consisting of methylcellulose, carboxymethylcellulose, hydroxypropylcellulose, gum arabic, tragacanth, sodium alginate, gelatin, carbomer, bentonite, solvents selected from the group consisting of water, alcohols or glycols, and stabilizers selected from the group consisting of polysorbate and castor oil polyoxyethylene ether or antioxidants selected from the group consisting of pyrosulfate sodium, ascorbic acid, wherein the composition further comprises compound 2-[(3Z)-6-fluoro-2-methyl-3-[(4-methylsulfinylphenyl) methylidene] inden-1-yl] acetic acid of the formula 1 in a unit dose in amount of 1-200 mg in combination with at least one pharmaceutical carrier, wherein the method of treatment comprises the following steps:
every day washing of wounds with 0.05% chlorhexidine solution or any other would disinfectant before treatment procedure to minimize wound contamination and infection,
applying the pharmaceutical composition in the volume of 200 μl/daily directly on the wound surface,
applying a sterile gauze for wound covering, and
washing a chamber cavity with 1 ml of sterile saline 3, 5 and 7 days after wounding under ether anesthesia.

* * * * *